(12) United States Patent
Weber et al.

(10) Patent No.: US 8,581,007 B2
(45) Date of Patent: Nov. 12, 2013

(54) USE OF STEAM TO REDUCE COKING AND/OR METAL DUSTING

(75) Inventors: Jörg F. W. Weber, Houston, TX (US); James O. Meredith, Hampshire (GB)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 13/404,441

(22) Filed: Feb. 24, 2012

(65) Prior Publication Data

US 2012/0253079 A1    Oct. 4, 2012

Related U.S. Application Data

(60) Provisional application No. 61/471,536, filed on Apr. 4, 2011.

(51) Int. Cl.
*C07C 45/51* (2006.01)

(52) U.S. Cl.
USPC .......................................... 568/402; 568/403

(58) Field of Classification Search
USPC .................................................. 568/402, 403
See application file for complete search history.

(56) References Cited

U.S. PATENT DOCUMENTS

| | | |
|---|---|---|
| 1,988,481 A | 1/1935 | Cardarelli |
| 4,224,298 A | 9/1980 | Robinson |
| 2003/0035766 A1 | 2/2003 | Baca et al. |
| 2003/0161785 A1 | 8/2003 | Dieckmann |
| 2006/0260982 A1 | 11/2006 | Yeung |

FOREIGN PATENT DOCUMENTS

| | | |
|---|---|---|
| EP | 1 464 910 | 10/2004 |
| EP | 1 582 510 | 10/2005 |

OTHER PUBLICATIONS

Jones, Richard T. et al., "Metal Dusting—An Overview of Current Literature", Corrosion 2001, Mar. 11-16, 2001, Houston, Tx. NACE.

*Primary Examiner* — Sikarl Witherspoon
(74) *Attorney, Agent, or Firm* — Andrew B. Griffis

(57) ABSTRACT

The invention is directed towards the reduction of coke formation in furnaces.

3 Claims, 2 Drawing Sheets

USE OF STEAM TO REDUCE COKING AND/OR METAL DUSTING

PRIORITY CLAIM

This application claims the benefit of U.S. Provisional Application No. 61/471,536, filed Apr. 4, 2011, the entirety of which is incorporated by reference.

FIELD OF THE INVENTION

The invention relates to the use of steam to reduce coking and/or metal dusting, particularly in the mitigation of heavy ends in the dehydrogenation of alcohols, and more specifically the production of methyl ethyl ketone (MEK) from sec-butyl alcohol (2-butanol or SBA).

BACKGROUND OF THE INVENTION

Conversion of sec-butyl alcohol (2-butanol or SBA) to methyl ethyl ketone (MEK) can be accomplished by vapor phase catalytic dehydrogenation of the alcohol at high temperature over metal oxide using a series of adiabatic reactors. Because the reaction is highly endothermic, the process stream is reheated between stages.

The dehydrogenation was conventionally carried out in furnace tubes packed with brass turnings. Later the process was changed to employ a series of adiabatic reactors packed with metal oxide deposited on calcined coke. The process stream was initially heated to 715-825° F. (380-440° C.) in the lead furnace. The stream was reheated in the second and third furnaces prior to being passed through the corresponding reactors. Overall conversions of 80-92 mol % were obtained with selectivities of SBA converted to MEK of 94-98 mol %.

The reaction is commercially valuable and constant attempts to improve conversion, selectivity, run time, and the like, are always being made. One of such attempts included the addition of liquid water to the dehydrogenation section feed stream in order to reduce the production of heavy end byproducts. This improved the selectivity to MEK but with some loss of activity and conversion.

The present inventors have determined that coke formed in the furnace tubes can build and spall with a result that coke particulates can appear in the heavier co-product fractions of the downstream product purification section. The present inventors have also surprisingly discovered that the injection of steam into the furnace coils reduces the problem of coke generation and subsequent spalling of coke particulates. In preferred embodiments, continuous injection of steam selectively added into only the last furnace coil in the SBA to MEK conversion section resulted in one or more of (i) lowered tube metal temperatures; and (ii) reduction of coke formation, with minimal impact on overall unit conversion.

In addition it has also been discovered that the presence of coke in the furnace tubes can initiate a corrosion mechanism called Metal Dusting, particularly when tube metal temperatures are in the range 795-1112° F. (424-600° C.). Accordingly, the present inventors also believe that application of the present invention can mitigate Metal Dusting.

SUMMARY OF THE INVENTION

The invention is directed towards the reduction of coke formation in furnaces, particularly in furnaces involved in the dehydrogenation of alcohols, such as the dehydration of sec-butyl alcohol (SBA) to methyl ethyl ketone (MEK), by injection of steam into one or more furnace coils. In preferred embodiments the alcohol is derived from an olefin.

The invention is also concerned with the lowering of tube metal temperatures by injection of steam into one or more furnace coils, with minimal impact on overall unit conversion.

In embodiments, there is a continuous injection of steam at very low rates into the last furnace coil in a series of furnaces in the dehydrogenation section of a system for the conversion of a starting material, preferably an alcohol, to a product, preferably a ketone.

In preferred embodiments, for the conversion of sec-butyl alcohol to methyl ethyl ketone in a series of adiabatic reactors, the injection of steam results in the introduction of approximately 1000 ppm to 7000 ppm additional water into the furnace coil feed streams.

It is an object of the invention to reduce the formation of coke in a furnace coil.

It is another object of the invention to reduce the phenomenon known as Metal Dusting, which causes corrosion of metal tubing in a system comprising one or more furnaces.

These and other objects, features, and advantages will become apparent as reference is made to the following detailed description, preferred embodiments, examples, and appended claims.

BRIEF DESCRIPTION OF THE DRAWINGS

In the accompanying drawings, like reference numerals are used to denote like parts throughout the several views.

DETAILED DESCRIPTION

The present invention is best explained by reference to a specific example, however one of skill in the art will recognize that the invention is applicable to any chemical conversion where build up of coke in a furnace and/or the phenomenon known in the art as Metal Dusting are problems.

Figure 1:
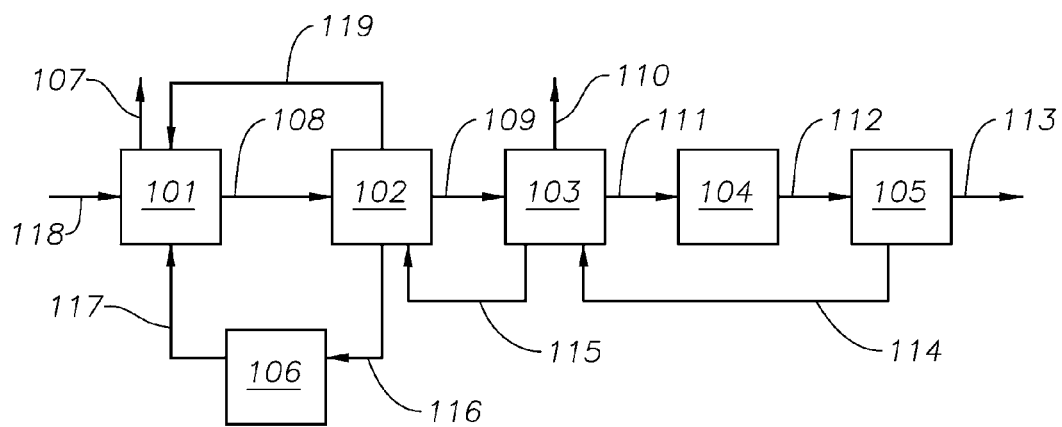
FIG. 1 is a schematic showing a process for the production of a ketone from an alcohol, in accordance with an embodiment of the present invention.
Figure 2:
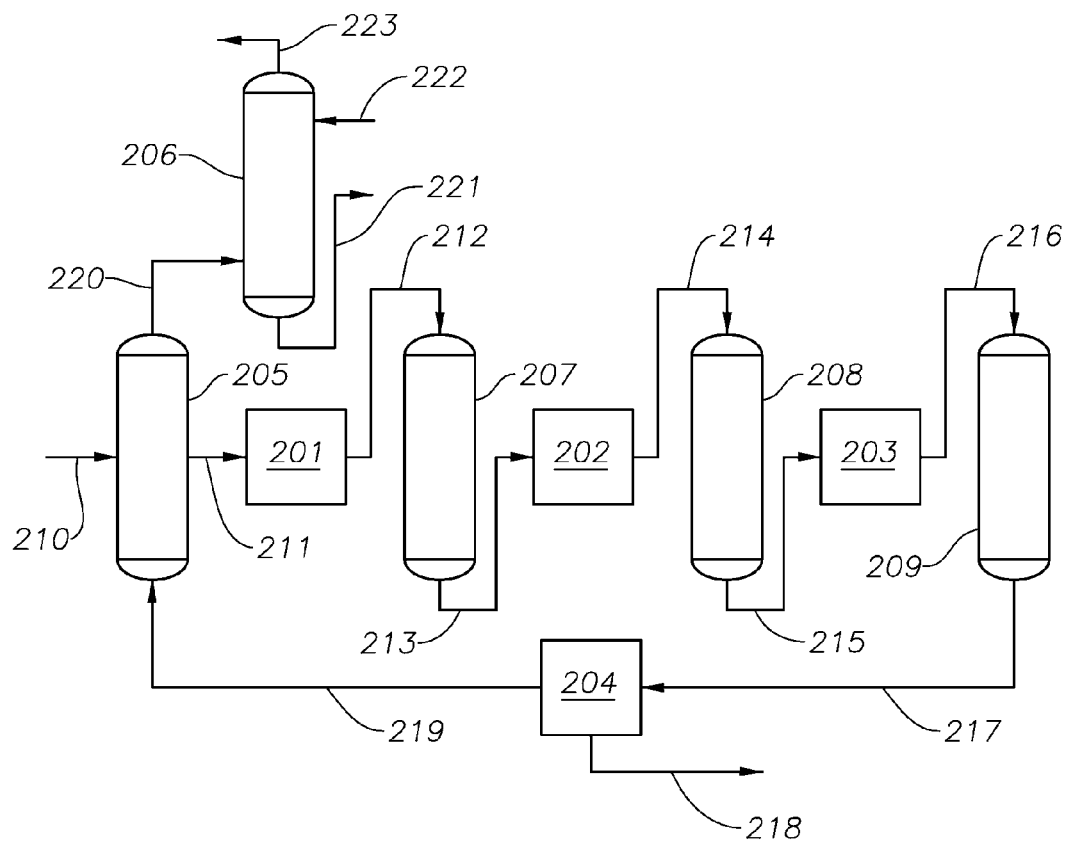
FIG. 2 is a schematic shown an aspect of FIG. 1, which includes the furnace coils involved in the conversion of alcohol to ketone according to the present invention.

MEK can be produced by vapor phase catalytic dehydrogenation of SBA in a process illustrated in a simplified schematic according to FIG. 1. A feedstream 118 comprising butenes is sent to the olefin contacting reactor 101 where the feedstream 118 is contacted with a stream 117 comprising acid from the acid concentrator 106. The product from 101 is sent to the SBA recovery section 102, where SBA is separated from butenes and spent acid which are recycled via conduits 119 and 116, respectively. The recovered SBA is sent via conduit 109 to the SBA finishing section 103 where finished SBA is separated from heavy & light byproducts, conduit 110 and aqueous slop SBA 115. The finished SBA is then sent via conduit 111 to SBA conversion section 104, the details of which are discussed below with respect to FIG. 2. Continuing with FIG. 1, the product of the conversion section 104 is crude MEK, which is sent via conduit 112 to MEK finishing section 105 and then purified MEK is recovered via conduit 113. Unreacted SBA and heavy by-products are recycled via conduit 114 to the SBA finishing section 103. FIG. 2 illustrates schematically the details of a typical SBA conversion section 104 in FIG. 1. The conversion of SBA to MEK is endothermic and produces hydrogen as a by-product via conduit 223. Reaction rates are maintained by plural sequential reaction and reheat steps. Shown in FIG. 2 are the sequential furnace coils 201, 202, and 203, in combination with reactors 207, 208, and 209, fluidly connected by conduits 212, 213, 214, 215 and 216, respectively. Finished SBA is introduced from conduit 210 to the alcohol scrubber 205, with Hydrogen containing little SBA taken overhead via 220 to water scrubber 206. Water is introduced to scrubber 206 via 222 and the SBA water is sent to the SBA finishing section 103 via 221 (connection not shown for convenience of view; see element 103 in FIG. 1). Hydrogen is removed overhead via conduit 223. Continuing with FIG. 2, $H_2$ containing little MEK is separated via 219 from flash drum 204 and scrubbed in alcohol scrubber 205 to recover light oxygenates. The crude MEK reactor product is send via conduit 218 to the MEK finishing section (see element 105 in FIG. 1) to remove light and heavy byproducts and unreacted SBA.

Different furnace configurations are possible: a) Three furnaces are equipped with one coil per furnace (3 furnaces/3 coils); b) One furnace is equipped with one coil and a second furnace is equipped with two coils (2 furnaces/3 coils); and c) One furnace is equipped with three coils (1 furnace/3 coils). Even 4 stage configurations have been used. Each coil can consist of a number of tubes in series or in parallel. The final choice of the number of furnace(s) and their coil designs is determined by the available system vapour pressure drop, the chosen number of heating and reaction steps, the total heat duty and the maximum allowable tube metal temperature.

Figure 3:
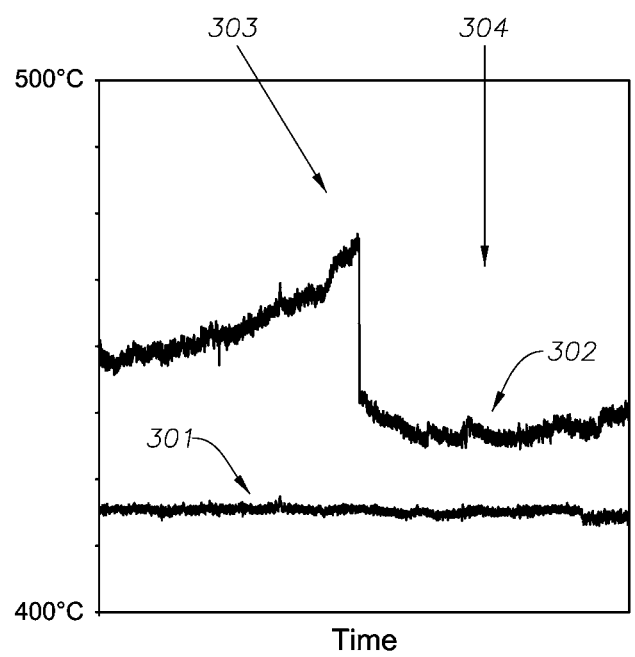
FIG. 3 shows the temperature profile of furnace coils inside the furnaces of a system according to the present invention.

FIG. 3 demonstrates the impact of steam injection into the last furnace coil in the last furnace in series (203 in FIG. 2). In FIG. 3, 301 and 302 show the tube metal temperature profiles of two individual tubes inside the middle furnace coil (202 in FIG. 2) and inside the last furnace coil (203 in FIG. 2), respectively. At a point in time denoted by arrow 303, a short burst of steam is injected into the coil in the last furnace. As shown in FIG. 3, the temperature of the coil drops dramatically. The tube metal temperature (TMT) profile in the middle coil 301 indicates a much more stable temperature profile without steam injection due to the lower temperature in the base case. Typically TMT's increase from the first tube in a coil to the last tube in a coil due to the increasing internal process temperature as the stream is heated. When coking occurs in a tube the TMT will further increase. As the process stream moves from reactor to reactor the concentration of MEK increases and the reactions that produce heavy byproducts and coke increase. Steam addition is therefore generally going to be more effective in the later stages of reaction; however, since coke dust is known to be present even the first stage it's highly likely that steam addition is beneficial in all stages. However, the downside is that the earlier that you use steam injection the more likely it will reduce the SBA to MEK activity and conversion. At the point in time denoted by arrow 304, continuous steam injection is commenced into the last coil in the last furnace. The instantaneous effect on the coil temperature is small, but the continuous injection keeps the coil tube metal temperature low. The total time shown on the x-axis of FIG. 3 is 19 days. The short burst of steam was for a time period of 15 minutes. The continuous steam injection was maintained for over 120 days with continued success. The amount of water in the product leaving the final reactor (209 in FIG. 2) should be kept at between 3000 ppm and 9000 ppm, in preferred embodiments.

Numerous mechanisms for the formation of coke during the series of reactions that occur from the feed to the final product for the schematic illustrated in FIGS. 1 and 2 can be postulated. Isobutenes and ketenes, among other side products that would be expected to exist in the reactors or conduits shown in the figures, are known precursors to coke, as are numerous cracking reactions of SBA and MEK. Aldol reaction products of MEK would be expected to exist in the reactors or conduits shown in the figures, are known precursors of coke. A shift in water gas shift equilibriums is known as another pathway for coke formation from carbon monoxide, carbon dioxide and hydrogen. Both aldol and water gas shift reactions are equilibrium reactions affected by changes in water concentration.

Metal dusting (MD) is a severe form of corrosive degradation of metals and alloys at high temperatures (300-850° C.) in carbon-supersaturated gaseous environments. Fe, Ni and Co, as well as alloys based on these metals are all susceptible. The corrosion manifests itself as a break-up of bulk metal to metal powder—hence the term, metal dusting. As with coking mechanisms, various mechanisms have been postulated for metal dusting. See, for instance, Journal of the Electrochemical Society, 154, 5, C231-C240, 2007.

Transmission electron microscopy (TEM) images of collected carbon particles from the top of a reactor bed in the last reactor in the series, in a system according to the schematic illustrations shown in FIGS. 1 and 2, show nano-sized $Fe_3C$ particles and filamentous carbon particles. $Fe_3C$ ruptures (and dissociates into Fe and C upon carbon deposition) and catalyzes formation of filamentous carbon. This is evidence of metal dusting in one, two or all three of the three furnace coils 201, 202, and/or 203 from one or both of the apparatus material or coke formation from the chemical reactants introduced in the feedstream. Without wishing to be bound by theory, the present inventors believe that metal dusting requires the deposit of carbon on the metal surface, this carbon could have been generated from CO, CO2, and other feed precursors discussed above. Otherwise coke formation is catalyzed by metal particles which could have been generated from metal dusting.

The controlled steam injection in the production of MEK selectively improves and suppresses heavy end reactions that can lead to such coking. The targeted addition of low rate steam injection into the later stage of the SBA to MEK conversion reaction, particularly when the steam is injected so as to produce a stream composition of 3000-9000 ppm water, suppressed such coking if present, thereby improving reaction selectivity with minimum impact on overall conversion and reduce furnace tube metal temperatures to reduce the base level coking and minimize the risk of initiation of metal dusting corrosion. The addition of steam is also beneficial in that it can slowly consume minor coke accumulation by water shift reactions, and limit or decrease any further increase in tube metal temperatures caused by the presence of coke.

A detailed study of selected coke samples taken from the unit concluded that the coke had a low H/C ratio with small transition metals and Iron impurities. Coking rates were quantified at approximately 2.5-12.5 g/tonne of Furnace feed. Multiple paths of investigation initially concluded that catalyst dust had migrated from reactor beds into the hot furnace tubes and had catalyzed the production of "sticky" MEK oligomers that became coke precursors. However, metallographic findings and site inspection findings confirmed the root cause of the tube corrosion attack to be metal dusting in the stainless steel and Chrome Moly furnace tubes, a special form of carburization, which produces aggressive pitting in the 450° C. to 850° C. tube metal temperature range.

Trade names used herein are indicated by a ™ symbol or ® symbol, indicating that the names may be protected by certain trademark rights, e.g., they may be registered trademarks in various jurisdictions. All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted. When numerical lower limits and numerical upper limits are listed herein, ranges from any lower limit to any upper limit are contemplated. While the illustrative embodiments of the invention have been described with particularity, it will be understood that various other modifications will be apparent to and can be readily made by those skilled in the art without departing from the spirit and scope of the invention.

What is claimed is:

1. In a process for the conversion of SBA to MEK by vapor phase dehydrogenation over a metal oxide catalyst in a system including a dehydrogenation zone comprising plural furnace coils, the improvement comprising the injection of steam directly into at least one of said furnace coils.

2. The process of claim 1, wherein said steam is process steam, and wherein said process steam is injected into said at least one furnace coil in an amount so that the MEK produced by said process comprises 3000-9000 ppm water.

3. The process of claim 1, wherein said steam is injected only into the last coil of said plural furnace coils.

* * * * *